United States Patent [19]
Lord et al.

[11] Patent Number: 6,102,901
[45] Date of Patent: Aug. 15, 2000

[54] ABSORBENT ARTICLE WITH HOOK FASTENERS

[75] Inventors: Patrick Robert Lord, Neenah; David Andrae Justmann, Hortonville, both of Wis.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 09/034,031

[22] Filed: Mar. 3, 1998

[51] Int. Cl.$^7$ ............................. A61F 13/15; A61F 13/20

[52] U.S. Cl. ............................................ 604/386; 604/391

[58] Field of Search .................................. 604/385.1, 386, 604/389, 390, 391

[56] References Cited

U.S. PATENT DOCUMENTS

| | | | |
|---|---|---|---|
| 2,477,914 | 8/1949 | Webb | 604/386 |
| 2,494,312 | 1/1950 | Rodgen et al. | 604/386 |
| 3,763,907 | 10/1973 | Hockley et al. | 604/391 |
| 3,901,236 | 8/1975 | Assarsson et al. | |
| 4,076,663 | 2/1978 | Masuda et al. | |
| 4,286,082 | 8/1981 | Tsubakimoto et al. | 526/240 |
| 4,663,220 | 5/1987 | Wisneski et al. | 428/221 |
| 4,699,823 | 10/1987 | Kellenberger et al. | 428/219 |
| 4,704,116 | 11/1987 | Enloe | 604/385 A |
| 4,753,646 | 6/1988 | Enloe | 604/385 R |
| 4,884,713 | 12/1989 | Handler | 220/23.4 |
| 4,887,338 | 12/1989 | Handler | 24/306 |
| 4,916,005 | 4/1990 | Lippert et al. | 428/192 |
| 4,938,753 | 7/1990 | Van Gompel et al. | 604/385.2 |
| 5,019,073 | 5/1991 | Roessler et al. | 604/391 |
| 5,226,992 | 7/1993 | Morman | 156/62.4 |
| 5,318,555 | 6/1994 | Siebers et al. | 604/390 |

(List continued on next page.)

FOREIGN PATENT DOCUMENTS 0 217 032 A3  4/1987  European Pat. Off. .

OTHER PUBLICATIONS

American Society for Testing Materials (ASTM) Designation: D 5169–91, "Standard Test Method for Shear Strength (Dynamic Method) of Hook and Loop Touch Fasteners," pp. 687–689, published Nov. 1991.

(List continued on next page.)

*Primary Examiner*—Mark O. Polutta
*Attorney, Agent, or Firm*—Paul Yee

[57] ABSTRACT

An absorbent article (10) has a first waistband portion (12), a second waistband portion (14) and an intermediate portion (16) interconnecting the front and back waistband portions. The article (10) comprises a backsheet layer (30), a liquid permeable topsheet layer (28) and an absorbent structure (32) which is sandwiched between the backsheet and topsheet layers. A fastening system is configured to operably connect the first waistband portion (12) to the second waistband portion (14) to hold the article on a wearer. The fastening system includes at least one fastener tab (36) attached to extend laterally at a side edge region (86) of the first waistband portion (12), and an articulated landing member (50) attached to the second waistband portion (14). The fastener tab (36) includes an extending layer member which has a predetermined clasping contour (60) formed therein, and the landing member has a moveable section (52) which is pivotably attached to the second waistband portion (14) of the article (10). A first mechanical fastener component (70), such as provided by a hook material, is attached to an appointed mating surface (54) of the moveable section (52). A second complimentary mechanical fasteners component (72), such as provided by a loop material, is attached to an appointed engagement surface section (58) of the second waistband portion (14), and the engagement surface section (58) is located substantially subjacent to the moveable section (52).

23 Claims, 5 Drawing Sheets

U.S. PATENT DOCUMENTS

| | | | |
|---|---|---|---|
| 5,399,219 | 3/1995 | Roessler et al. | 156/259 |
| 5,486,166 | 1/1996 | Bishop et al. | 604/366 |
| 5,490,846 | 2/1996 | Ellis et al. | 604/366 |
| 5,540,796 | 7/1996 | Fries | 156/164 |
| 5,562,650 | 10/1996 | Everett et al. | 604/378 |
| 5,595,618 | 1/1997 | Fries et al. | 156/164 |
| 5,605,735 | 2/1997 | Zehner et al. | 428/100 |
| 5,624,429 | 4/1997 | Long et al. | 604/391 |
| 5,662,641 | 9/1997 | Gulsby | 604/389 |

OTHER PUBLICATIONS

American Society for Testing Materials (ASTM) Designation: D 5170–91, "Standard Test Method for Peel Strength ("T" Method) of Hook and Loop Touch Fasteners," pp. 690–692, published Nov. 1991.

TAPPI Official Test Method T 543 om–94, "Bending Resistance of Paper (Gurley Type Tester)," published by the TAPPI Press, Atlanta, Georgia, pp. 1–5.

Federal Test Method Standard (FTMS) No. 191A, Method 5514, "Water Resistance of Cloth; Low Range, Hydrostatic Pressure Method," Jul. 20, 1978, 3 pages.

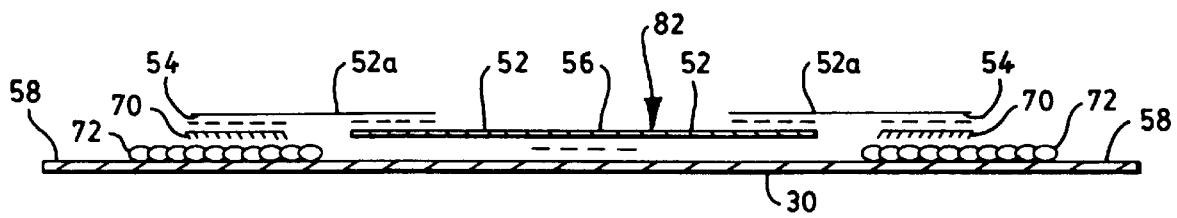
FIG. 6
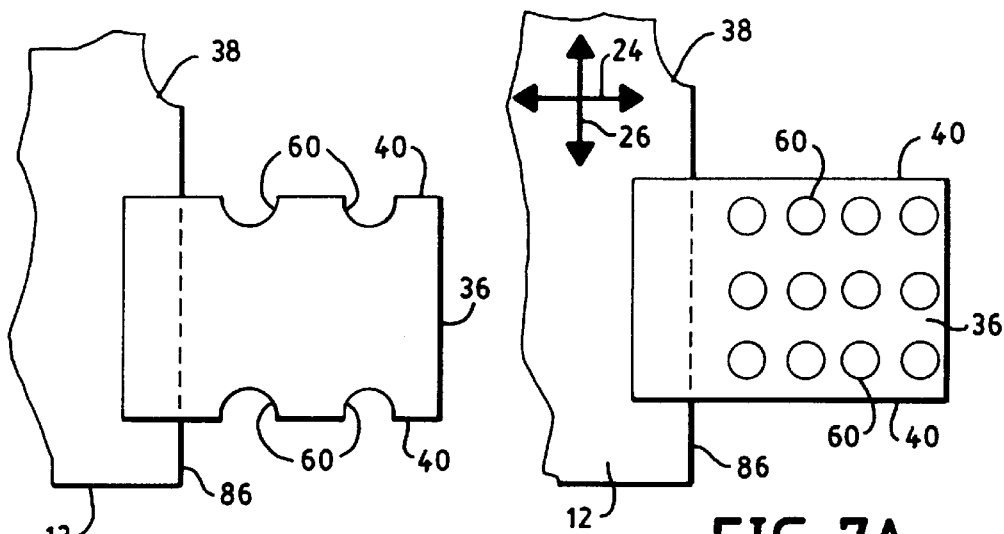
FIG. 7
FIG. 7A
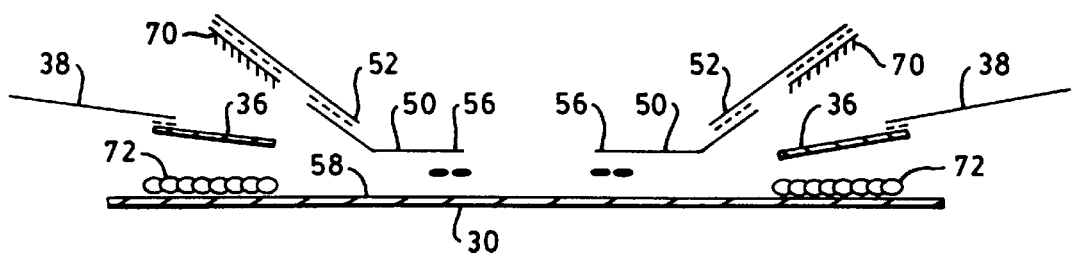
FIG. 8

6,102,901

ABSORBENT ARTICLE WITH HOOK FASTENERS

FIELD OF THE INVENTION

The present invention relates to garment articles. More particularly, the present invention relates to absorbent articles, especially disposable absorbent articles, which have more secure fastening with improved fit and performance.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configuration of waist elastics, leg elastics, elasticized liners, and elasticized outercovers have been employed on garment articles to help produce and maintain the fit of the articles about the body contours of the wearer.

Conventional garment articles, such as those described above, have not provided desired levels of reliable fit, and have susceptible to excessive sagging and drooping during the period of wearing. The garment structures have not adequately maintained the desired levels of fit and comfort, and where the garments are configured as absorbent articles, the articles have been susceptible to excessive leakage of liquids and other waste materials. As a result, there has been a continued need for improved garments having more consistent fit and greater resistance to sagging and drooping.

BRIEF DESCRIPTION OF THE INVENTION

Generally stated, the present invention provides a distinctive article which includes a first waistband portion, a second waistband portion and an intermediate portion which interconnects the front and back waistband portions. The article comprises a backsheet layer, a liquid permeable topsheet layer connected in superposed relation with the backsheet layer, and an absorbent structure which is sandwiched between the backsheet and topsheet layers. A fastening system connects the first waistband portion to the second waistband portion to hold the article on a wearer. The fastening system includes at least one fastener tab attached to extend laterally at a side edge region of the first waistband portion, and an articulated landing member joined to the second waistband portion. The fastener tab includes an extending layer member having a clasping contour formed therein, and the landing member has a moveable section pivotably attached to the second waistband portion of the article. A first fastener component is attached to an appointed mating surface of the moveable section of the landing member, and a cooperating second fastener component is attached to an appointed surface section of the second waistband portion. The appointed surface section is located substantially subjacent to the moveable section.

By incorporating its various aspects, the article of present invention can provide more reliable and more consistent fit about the wearer with greater resistance to sagging and drooping. The desired fit can be better maintained even when the wearer is highly active. Where the garment is an absorbent article, the improved resistance to drooping can reduce gapping between the garment and wearer, and can reduce the leakage of liquid or semi-liquid waste materials.

BRIEF DESCRIPTION OF THE DRAWINGS

The present invention will be more fully understood and further advantages will become apparent when reference is made to the following detailed description of the invention and the drawings, in which:

FIG. 6 representatively shows an expanded, transverse cross-sectional view of a fastening system wherein a cap member provides a laterally opposed pair of landing members;

FIG. 7 representatively shows a top view of a fastener tab which can be employed with the invention;

FIG. 7A representatively shows a top view of another fastener tab which can be employed with the invention;

FIG. 8 representatively shows a further cross-sectional view of the fastening system of FIG. 5, as arranged to provide its fastening inter-engagements;

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

Figure 1:
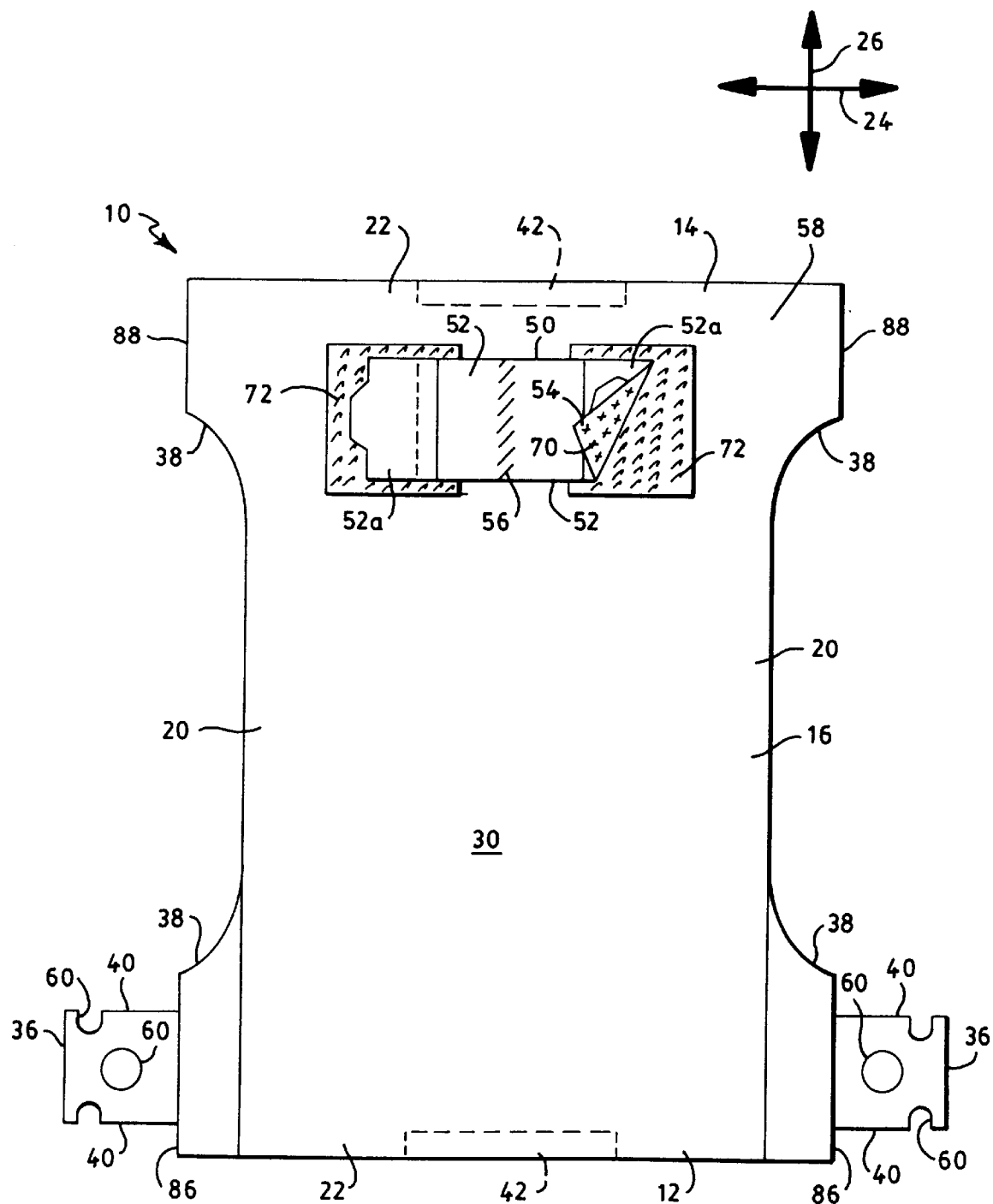
FIG. 1 representatively shows a top view of an outerside of the article of the invention.
Figure 2:
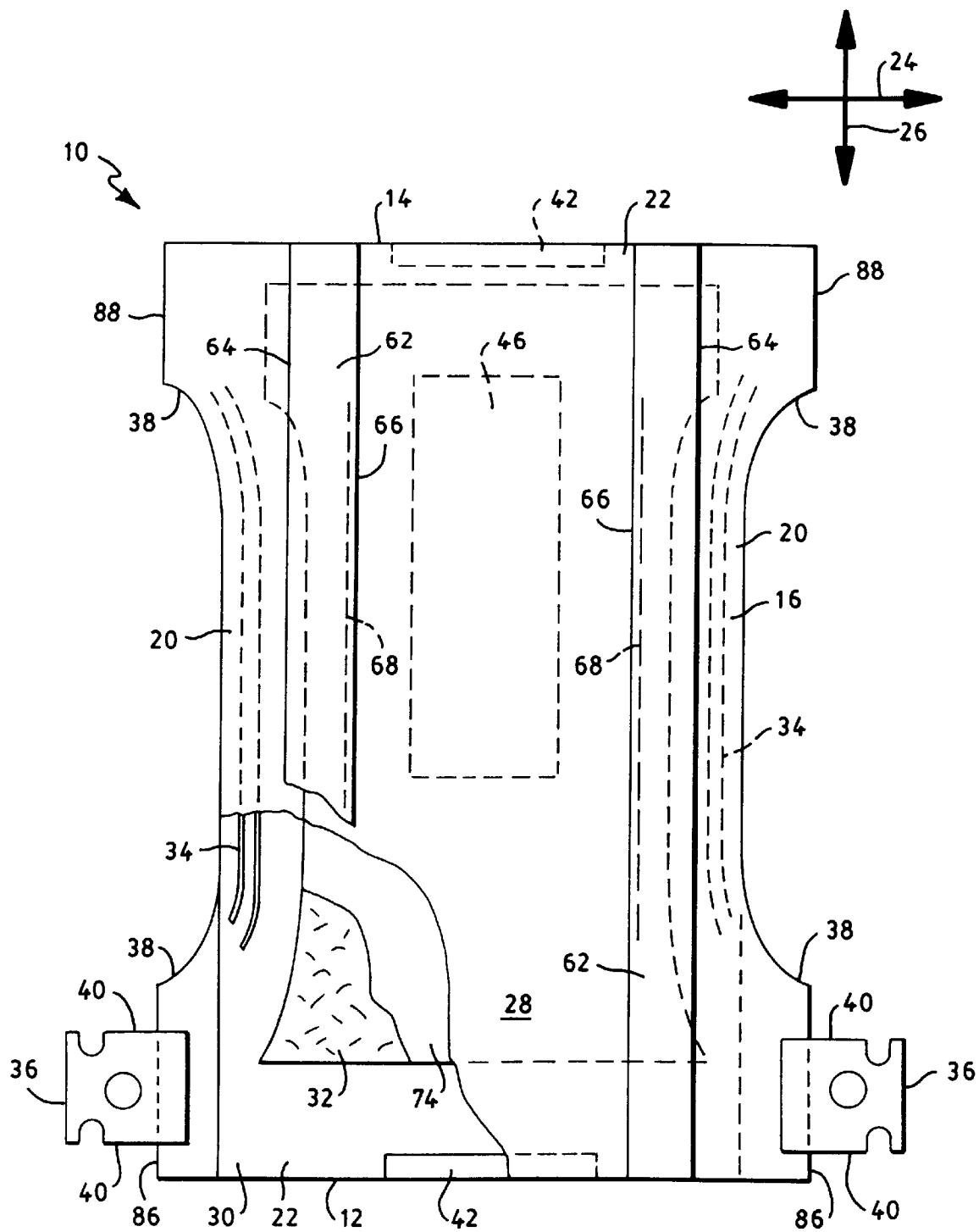
FIG. 2 representatively shows a partially cut-away, top view of a bodyside of the article of the invention.
Figure 3:
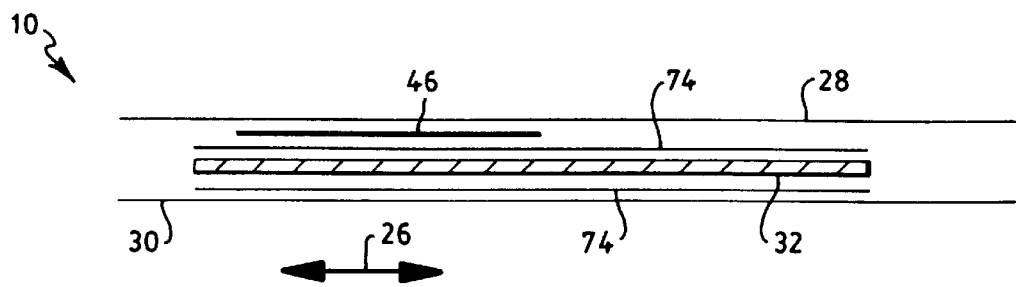
FIG. 3 representatively shows an expanded, longitudinal cross-sectional view of the article shown in FIG. 2.

With reference to FIGS. 1, 2 and 3, an article, such as the representatively shown absorbent article of diaper 10, has a length-wise longitudinal direction 26, a transverse, lateral direction 24, and a first waistband portion 12, such as the waistband section at the back or rear of the diaper. The first waistband portion has an inward, bodyside surface and an outward surface thereof. A second waistband portion 14, such as the waistband section at the front of the diaper, is positioned longitudinally opposite of the first waistband portion 12 and has an inward, bodyside surface and an outward surface thereof. An intermediate, crotch portion 16 interconnects the first and second waistband portions 12 and 14, respectively. The article comprises a backsheet layer 30 which has an outward surface and an opposed, inward or bodyside surface thereof. As representatively shown, the outward surface of the backsheet layer may provide the outward surface of the article. A substantially liquid permeable topsheet layer 28 is connected in a superposed relation with the backsheet layer 30, and an absorbent structure 32 is sandwiched between the backsheet and topsheet layers. A distinctive fastening system is constructed and arranged to interconnect the first waistband portion 12 with the second waistband portion 14 to hold the article on a wearer. The fastening system includes at least one fastener tab 36 attached to extend laterally at a side edge region 86 of the first waistband portion 12, and a flexible, pivotably connected or otherwise articulated landing member 50 is joined to the second waistband portion 14. In the shown configuration, for example, the landing member can be attached directly to the second waistband portion of the backsheet member 30. The fastener tab 36 includes an extending layer member which has a clasping contour 60 formed therein, and the landing member has a flap-like moveable section 52 which is pivotably attached to the second waistband portion 14 of the article 10. A first fastener component 70, such as a first mechanical fastener component which includes the illustrated hook element material, is attached to an appointed mating surface 54 of the moveable section 52, which in the representatively shown configuration, is an inwardly facing surface of the landing member 50. A cooperating second fastener component 72, such as a second mechanical fastener component which includes the illustrated loop element material, is attached to an appointed, engagement surface section of the second waistband portion 14. The appointed surface section is located substantially subjacent to the moveable section 52, and in the representatively shown arrangement, the appointed engagement surface section is an outward surface 58 of the second waistband portion, such as may be provided by an outward surface of the backsheet member 30.

The various aspects (individually and in combination) of the present invention can advantageously help to better maintain the desired fit around the wearer. For example, the aspects of the invention can help reduce the sagging and drooping of the crotch region of the garment, and can help reduce roll-over and drooping at the waist region. When incorporated into an absorbent article, the various aspects of the invention can improve fit and appearance, and can reduce undesired gapping and leakage.

A desired garment article of the invention can, for example, be the representatively shown disposable diaper 10. The diaper can include a backsheet layer 30, a liquid permeable topsheet layer 28 connected and integrated with the backsheet layer, and an absorbent structure, such as a structure which includes absorbent body 32. The absorbent structure is sandwiched between the backsheet and topsheet layers, and is operably held therebetween. A fastening system, such as a system including fasteners 36, is configured to join the first, back waistband portions 12 in an overlapping relation with the second, front waistband portion 14 to thereby encircle the wearer's body and hold the diaper secure on the wearer during use. Optionally, the fastening system can employ fastener tabs 36 which are configured to join the front waistband portion 14 in an overlapping relation with the back waistband portions 12 to thereby encircle the wearer's body during use.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing zone member 50 which is disposed on the outward surface 92 of the article. In the configuration shown in FIGS. 1 and 2, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

FIGS. 1 and 2 show typical plan views of the representative disposable diaper 10 in its generally flat-out, uncontracted state (i.e., with substantially all elastic induced gathering and contraction removed). Portions of the structure are partially cut away to more clearly show the interior construction of the diaper article, and the bodyside surface of the diaper which contacts the wearer is facing the viewer. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward surfaces are configured to face toward the body of the wearer when the article is placed about the wearer. The outward surface of the article is configured to face away from the wearer's body when the article is placed about the wearer.

The diaper 10 typically includes a porous, liquid permeable topsheet 28; a substantially liquid impermeable backsheet 30; an absorbent structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with a retention portion of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which issued as U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which issued as U.S. Pat. No. 5,595,618. The disclosures of the above-described documents are incorporated herein by reference in a manner that is consistent (not in conflict) herewith.

Diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worm, wholly or partially cover or encircle the waist or mid-lower torso of the wearer. The intermediate, crotch region 16 lies between and interconnects the waistband regions 14 and 12, and comprises that portion of the diaper which, when worm, is positioned between the legs of the wearer and covers the lower torso of the wearer. Thus, the intermediate crotch region 16 is an area where repeated fluid surge typically occur in the diaper or other disposable absorbent article.

Backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES® SUPREME diaper, which is commercially available from Kimberly-Clark Corporation. The backsheet 30 typically provides the outer cover of the article. Optionally, however, the article may include a separate outer cover component member which is additional to the backsheet.

Backsheet 30 may alternatively include a micro-porous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment means may also be employed to suitably interconnect, assemble and/or affix together the various other component parts of the articles which are described herein.

The absorbent body 32 provides an absorbent structure which can include a retention portion, such as the shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges of liquid that may be introduced into the absorbent body of the article. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which issued as U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which issued as U.S. Pat. No. 5,490,846; the entire disclosures of which are hereby incorporated by reference in a manner that is consistent herewith.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized leg-band.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like.

For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 82 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May. 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), now U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995 (attorney docket No. 11,091), the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more, appointed landing member regions or patches, such as provided by the representatively shown, primary landing members 50. Each landing member 50 can provide an operable target area for generating a releasable and re-attachable securement of at least one of the fastener tabs 36 therewith. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Figure 4:
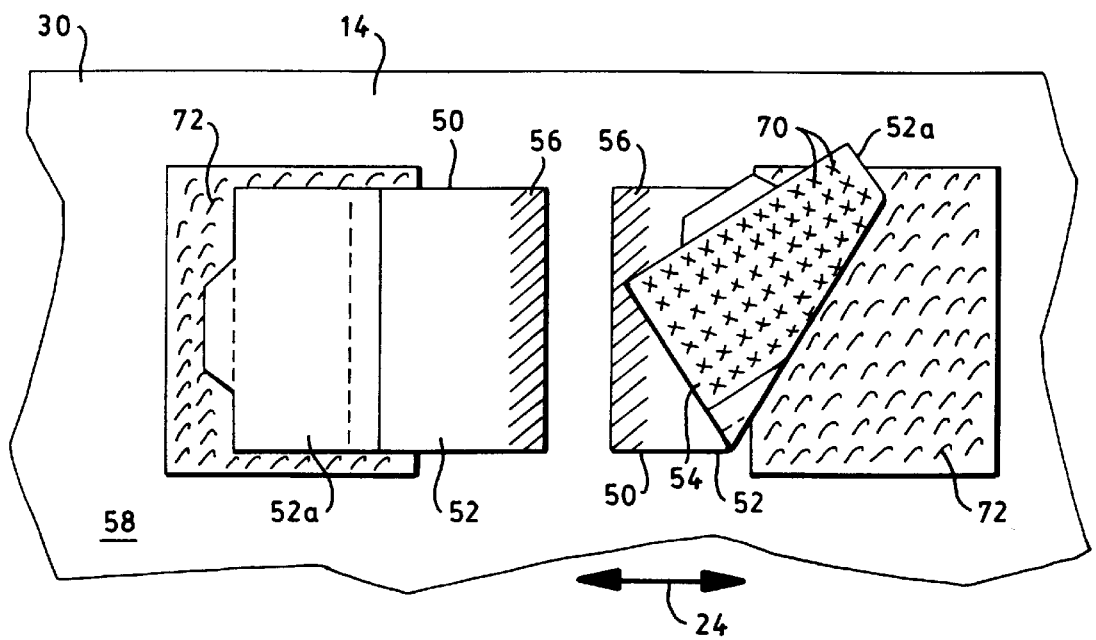
FIG. 4 representatively shows a partially open, top view of an embodiment of the fastening system of the invention having two, laterally opposed landing members.
Figure 5:
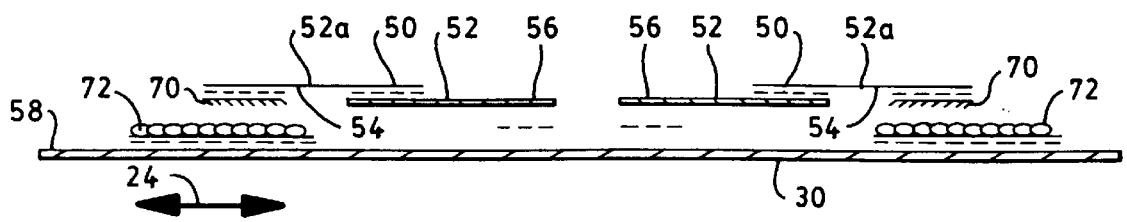
FIG. 5 representatively shows an expanded, transverse cross-sectional view of the fastening system illustrated in FIG. 4.

With reference to the desired configurations representatively shown in FIGS. 4 and 5, the article fastening system can include a laterally opposed pair of landing members 50.

Each landing member 50 includes a base section 56 which is joined and affixed to the appointed surface of the article, and a movable section 52 which is movably attached to the base section 56 with a flexible, pivotable or otherwise articulated joint to provide an operative, articulated landing member 50. Each movable section 52 may be a unitary piece or may include a plurality of component sections. As representatively shown, for example, each movable section 52 can include a supplemental extension member 52a which extends laterally outward and away from the centerline of the article. A selected, first fastener component 70 is attached to an appointed mating surface 54 of each of the movable sections 52. It should be readily appreciated that the representatively shown pair of landing members 50 could optionally be assembled or otherwise joined together to effectively form an integrated cap member 82, as representatively shown in FIG. 6.

Particular arrangements of the invention can include landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. the representatively shown configuration, the selected, second fastener component 72 can be located at a cooperating pair of appointed engagement areas of the second waistband portion 14. Each engagement area is associated with an appointed one of the landing members 50. When each landing member movable section 52 is pivoted to lie substantially flat against the article (e.g. FIG. 6), at least a portion of each engagement section of the second fastener component 72 is operably positioned to be immediately adjacent to the first fastener component 70 located on the movable section 52 of its associated landing member 50.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

A configuration which employs a releasable, interengaging mechanical fastening system can, for example, locate a first component having a first element of the mechanical fastener on at least the mating surface of the movable section 52 of the landing member 50, and can locate a second component having a cooperating, second element of the mechanical fastener on the engagement surface of the second waistband portion 14 of the article. For example, with the representatively shown hook-and-loop fastener, the hook material can be operably connected and affixed to the movable section of the landing member 50, and the loop material can be operably connected and affixed to the appointed engagement surface of the second waistband portion. Alternatively, the loop material can be operably connected to the landing member 50, and the hook material can be operably connected to the appointed engagement surface of the second waistband portion.

In the various configurations of the invention, at least one separately provided tape fastener tab 36 can be located at either or both of the lateral end regions 86 of the back waistband 12. Alternatively, a separately provided tape fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to extend from a corresponding, immediately adjacent ear region joined at one of the opposed lateral ends of the rear waistband section 12.

In the representatively shown configuration, the front waistband region is configured to provide an overlapping relation with the rear waistband region when the article is worn. Alternatively, the article can have a construction wherein the rear waistband region is configured to provide overlapping relation with the front waistband region when the article is worn. In such alternative arrangement, the front waistband region may be identified as the first waistband portion 12 and the rear waistband region may be identified as the second waistband portion 14.

The fastener tab 36 can be composed of a substantially non-elastomeric material, such as polymer films or tapes, woven fabrics, nonwoven fabrics or the like, as well as combinations thereof. In particular aspects of the invention, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

With reference to FIGS. 1 and 2, a lateral end of at least one fastening tab 36 can be affixed to extend laterally from at least one side edge region of at least one of the waistband portions 12 and 14. In a desired configuration, at least one fastening tab 36 is attached to extend laterally at each of a pair of laterally opposed side edge regions 86 of the first waistband portion 12. In addition, each fastening tab includes a clasping contour formed into the tab material. The clasping contours can include apertures, indentations and other types of openings, as well as combinations thereof. Additionally, the openings may be configured with various combinations of sizes and shapes, as desired.

In a particular aspect of the invention, the clasping contour 60 can be provided by at least one aperture formed through the layer member of the fastener tab 36, as representatively shown in FIG. 1. In other aspects, the clasping contour 60 can be provided by a plurality of apertures formed through the fastener tab, as representatively shown in FIG. 7A.

In particular aspects, the apertures formed through the layer member of the fastener tab 36 can be circular with a diameter of up to about 2 inches (about 5.1 cm). Alternatively, the apertures may be non-circular, and may be regular or irregular in shape, as desired to provide operative and improved levels of fastening engagement.

In other aspects, the apertures formed through the fastener tab 36 can be arranged in an irregular or regular pattern. For example, the apertures may be arranged in rows which are aligned in the longitudinal direction 26 and/or the lateral direction 24, as desired to provide selected levels of fastening engagement.

In a further aspect of the invention, the clasping contour 60 can be provided by at least one indentation formed into at least one laterally extending, longitudinal side edge 40 of the layer member of the fastener tab 36. As representatively shown in FIGS. 1 and 7, the clasping contour 60 can be provided by a plurality of indentations formed into a pair of longitudinally opposed, laterally extending side edges 40 of the fastener tab 36.

The indentations formed into the side edges 40 of the fastener tab 36 can have the following dimensions. Along the lateral dimension 24 of the side edges 40, each individual indentation can have a cross-directional extent of at least a minimum of about 0.5 cm. The cross-directional extent can alternatively be at least about 1 cm, and can optionally be at least about 1.5 cm to provide improved performance. In other aspects, each indentation can have a cross-directional length of not more than a maximum of about 5 cm. The cross-directional length can alternatively be not more than about 3 cm, and can optionally be not more than about 2 cm to provide improved performance. Along the longitudinal direction 26, each indentation can extend into the tab material to a depth distance of at least about 0.5 cm. The depth can alternatively be at least about 0.7 cm, and can optionally be at least about 0.8 cm to provide improved performance. In other aspects, each of the indentations can have a depth distance of not more than a maximum of about 2 cm. The depth can alternatively be not more than about 1.5 cm, and can optionally be not more than about 1 cm to provide improved performance.

In further aspects, the indentations can be arranged in an irregular or regular pattern, or can include a selected distributions of sizes and/or shapes. For example, the arranged pattern can be configured with relatively smaller-sized indentations located at the laterally distal region of the fastener tab 36, and relatively larger-sized indentations located at the laterally inboard regions of the fastener tab. In particular arrangements, the size of the indentations can progressively increase in three or more stages of a selected sizing gradient as the locations of the observed indentations moves laterally inboard from the laterally distal edge of the fastener tab 36. Alternatively, the size of the indentations can progressively decrease in accordance with selected sizing pattern as the locations of the indentations moves laterally inboard from the laterally distal edge of the fastener tab 36.

The operation of the fastening system is representatively shown in the schematic of FIG. 8. During the operation, the fastener tab 36 is interposed and effectively sandwiched between the first mechanical fastener component 70 and its associated second mechanical fastener component 72. The first mechanical fastener component 70 is configured to operably engage the second mechanical fastener component 72 within and through at least a portion of the clasping contour 60 of the fastener tab 36 when the mating surface 54 of the movable section 52 of the landing member 50 is positioned in a mating, engagement contact with the appointed outward surface section 58 of the second waistband portion 14. In the illustrated arrangement, the hook elements on the movable section and the loop elements on the outer surface of the second waistband portion can releasably attach to one another through the open areas bounded or otherwise exposed by the clasping contours 60. The inter-engagement between the first and second fastener components can thereby trap and substantially prevent undesired movement of the fastener tab away from the laminated, sandwiched assembly when the article is worn.

Figure 9:
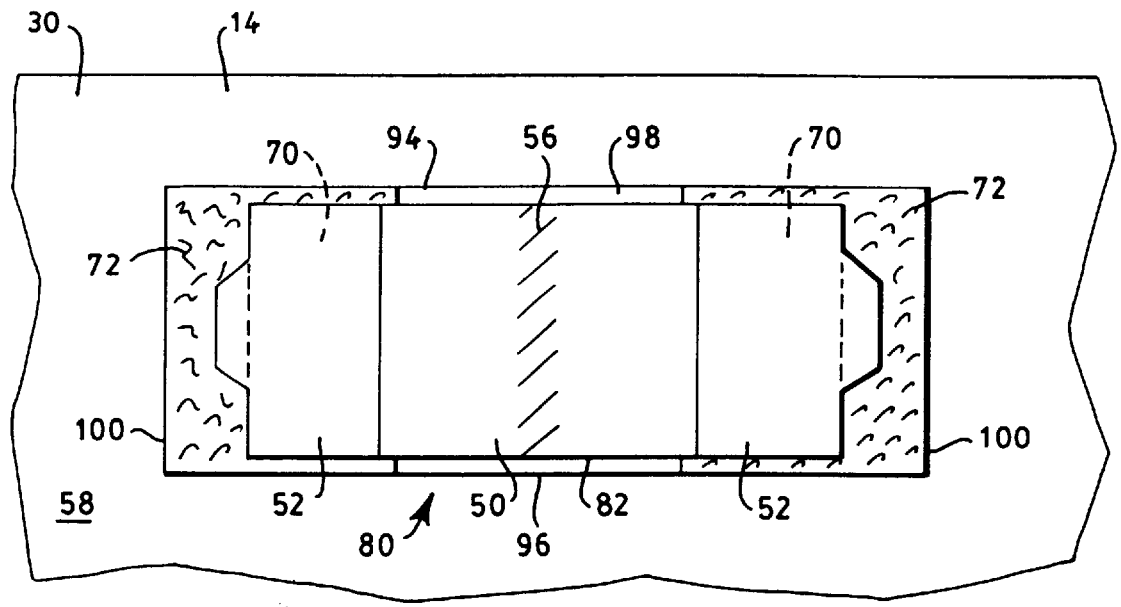
FIG. 9 representatively shows a top view of another embodiment of the fastening system of the invention having a composite landing zone member.
Figure 10:
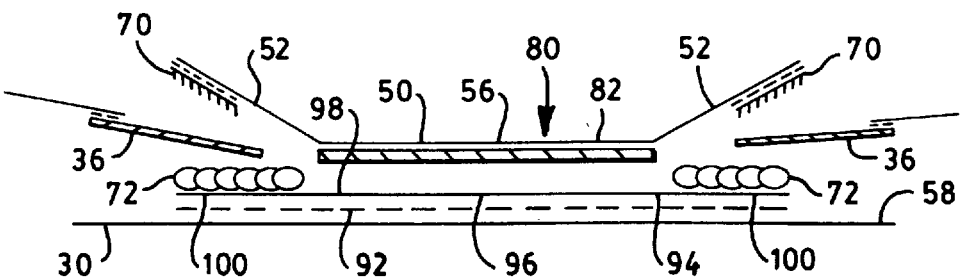
FIG. 10 representatively shows an expanded, transverse cross-sectional view of the fastening system illustrated in FIG. 9 positioned to provide its fastening inter-engagements with the fastener tab.
Figure 11:
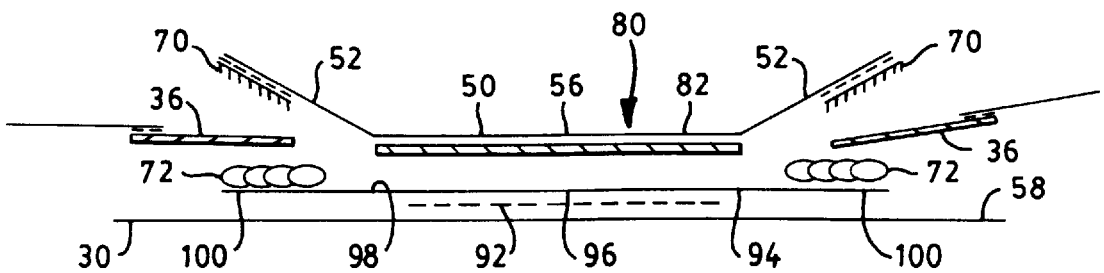
FIG. 11 representatively shows a cross-sectional view of another fastening system wherein the second fastener component is movably connected to its appointed waistband portion of the article.

With reference to FIGS. 9, 10 and 11, another aspect of the invention can include a composite landing member 80 which can be configured to provide a laterally opposed pair of landing members 50 with a substantially contiguous, interconnected configuration. A particular aspect of the fastening system can have a composite landing member 80 which includes a cap member 82 and a pair of wing-like, moveable sections 52. The cap member 82 can further have a medial base section 56 attached to the second waistband portion 14. The moveable sections 52 are pivotably attached to the medial base section 56 of the cap member 82, and an area of the first mechanical fastener component 70 is attached to an appointed mating surface 54 of each movable wing section 52.

A further aspect of the invention can have a composite landing member 80 which includes a carrier member 94 which is attached to the second waistband portion 14 of the article and is interposed between the cap member 82 and the backsheet layer 30. The carrier member 94 includes at least a medial region 96 thereof which is attached to the medial, base section 54 of the cap member 82. With reference to FIG. 11, at least a medial section of the carrier member 94 is attached to the outward surface of the article, such as the outward surface of the part of the backsheet layer 30 located at the second waistband portion 14 of the article, with a suitable attachment mechanism 92. Alternatively, a substantial entirety of the lateral extent of the carrier member 94 can be affixed to the backsheet layer, as representatively shown in FIG. 10. In the various configurations, an area of the second mechanical fastener component 72 is attached to an outward surface 98 of a laterally opposed pair of end regions 100 of the carrier member 94. Accordingly, the second fastener component can be operably joined to the second waistband portion with an indirect attachment system.

The carrier member 96 can be composed of a substantially non-elastomeric material, such as polymer films, woven fabrics, nonwoven fabrics or the like, as well as combinations thereof. In particular aspects of the invention, carrier member may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

The pair of end regions 100 of the carrier layer member 94 may be attached to the second waistband portion 14 of the article. In an alternative aspect of the invention, however, the pair of end regions 100 of the carrier layer member 94 are substantially unattached to the second waistband portion 14 of the article. As a result, the configuration can provide more flexible, self-aligning securement, and can help reduce the drooping of the front waistband of the diaper.

In particular arrangements, the first mechanical fastening component 70 can be a hook material, and the second mechanical fastening component 72 can be a loop material. In alternative configurations, the first mechanical fastening component 70 can be a loop material, and the second mechanical fastening component 72 can be a hook material.

In a further aspect of the invention, the cap member 82, and particularly the wing sections 54 of the cap member, can be constructed with an elastomeric material which is elastomerically stretchable at least along the lateral direction 24 of the article.

In another aspect of the invention, the carrier member 94 particularly the carrier member end regions 100, can be composed of an elastomeric material which is elastomerically stretchable at least along the lateral direction 24 of the article.

During the operation of the various configurations of the fastening system, at least the portion of the fastener tab 36 which includes the clasping contour 60 is interposed between the first mechanical fastener component 70 positioned on the mating surface 54 of the landing member movable section 52, and the second mechanical fastener component 72, which is operatively joined and attached to the outward surface section 58 of the front waistband portion 14 of the backsheet layer 30. Each movable section 52 can then be pivoted about an associated axis line, or other operative region, of generally rotational movement to contact the interposed fastener tab 36. The fastening elements of the first mechanical fastener component 70 which thereby become aligned with the apertures or other clasping contours in the fastener tab 36 can then communicate through the clasping contours of the tab to contact and operatively engage the cooperating elements of the second mechanical fastener component 72 which are suitably aligned with the clasping contours. Thus, the operative engagement occurs through the clasping contours and extends through the thickness dimension of the layer material of the fastener tab 36. As a result, the fastener tab can be operatively clamped between and effectively pinned by the inter-engaging, first and second fastener components. At least a portion of the cooperatively engaged elements of the first and second fastener components can thereby contact, abut and otherwise engage the terminal edges of the clasping contours to operably secure the fastener tab against undesired, further movement.

In the various configurations of the invention, the first and/or second fastening component may include an adhesive fastening mechanism, a cohesive fastening mechanism, or the like, as well as combinations thereof. Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components. As shown in the illustrated arrangements, for example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single or multiple hook configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

In desired arrangements of the invention, the fastening component, which is attached to the appointed mating surface of the moveable section 52 of the landing member may include a hook type of mechanical fastening element, and the complementary fastening component, which is operably joined and attached to an appointed outward surface section 58 of the second waistband portion (such as by being attached to the end regions 100 of the carrier member), can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the moveable section 52 of the landing member may include a loop type of mechanical fastening element, and the complementary fastening component, which is operatively joined and attached to an appointed outward surface section 58 of the second waistband portion (such as by being attached to at least the end regions 100 of the carrier member), can include a hook type of fastening element.

Examples of suitable hook-and-loop fastening systems are described in U.S. Pat. No. 5,019,073 issued May. 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which issued as U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 (attorney docket No. 12,563), the entire disclosure of which is hereby incorporated by reference in a manner which is consistent herewith.

In the various aspects and configurations of the invention, the hook element material can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N.H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensborough, N.C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

In particular aspects of the invention, the loop material need not be limited to a discrete or isolated patch on the outward surface of the article. Instead, the loop material can, for example, be provided by a substantially continuous, outer fibrous layer which is integrated to extend over substantially the total exposed surface area of a cloth-like outer cover employed with the diaper 10.

In the various configurations of the invention, the engagement force between the selected first fastener component and its appointed and cooperating second fastener component should be large enough and durable enough to provide an adequate securement of the article on the wearer during use. In desired configurations, the engagement force can provide a peel force value of not less than about 75 grams-force (gmf). Alternatively, the peel force is not less than about 100 gmf, and optionally is not less than about 400 gmf. In particular aspects, the peel force is not more than about 1,200 gmf. Alternatively, the peel force is not more than about 800 gmf, and optionally is not more than about 600 gmf to provide improved benefits.

The engagement force can additionally provide a shear force value of not less than about 1,000 gmf. Alternatively, the shear force is not less than about 2,000 gmf, and optionally, is not less than about 3,000 gmf. In further aspects, the shear force is not more than about 10,000 gmf. Alternatively, the shear force is not more than about 9,000 gmf, and optionally is not more than about 8,000 gmf to provide improved performance.

The peel force value can be determined in accordance with standard procedure ASTM D5170, approved Sep. 15, 1991 and published November 1991; with the following particulars. The test specimen width is 1.125 inch, and the specimen length is 2.3 inch. The roller device weighs 4.5 pounds and includes a rubber coating around the roller circumference. A suitable roller is part number HR-100 available from Chemsultants International, a business having a location in Mentor, Ohio. During the engagement of the fastener components, the roller is rolled over the test specimen through one cycle. During testing, the fastener material held by the stationary clamp can be larger in area, as compared to the fastener material held in the moving clamp. The initial separation distance between the clamps of the tensile tester is 4 inch, and the extension speed of the tensile testing machine is 20 inch/min. The reported value of a peel test result is a "three-peak average" value.

The shear force value can be determined in accordance with the standard procedure ASTM D-5169, approved Sep. 15, 1991 and published November 1991 with the following particulars. The test specimen width is 1.125 inch, and the specimen length is 2.3 inch. The roller device weighs 4.5 pounds and includes a rubber coating around the roller. A suitable roller is part number HR-100 available from Chemsultants International, a business having a location in Mentor, Ohio. During testing, the fastener material (e.g. the loop material) held by the stationary clamp can be larger in area, as compared to the fastener material (e.g. hook material) held in the moving clamp. The initial separation distance between the clamps of the tensile tester is 4 inch, and the extension speed of the tensile testing machine is 10 inch/min.

The particulars of the standard test procedures are intended to generate fastening conditions that can be more representative of consumer use conditions. When preparing the test specimen materials (e.g. hook and loop materials) for determining their cooperating peel or shear force value, it should be noted that the width dimension of the selected specimen material will correspond to the dimension of the fastener material which, in the actual article, is found to be aligned along the longitudinal direction 26 of the article. Similarly, the length dimension of the selected specimen material will correspond to the dimension of the fastener material which, in the actual article, is found to be aligned along the lateral direction 24 of the article.

In addition, the securing engagement between the first and second fastener components should be sufficient to prevent a disengagement of the fastener tab 36 away from the landing member 50 when the fastener tab 36 is subject to a tensile force of at least about 5,000 grams when the tensile force is applied outwardly along the lateral direction, aligned generally parallel with the plane of the backsheet layer 30 of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a first waistband portion, a second waistband portion and an intermediate portion interconnecting said front and back waistband portions, said article comprising:

a backsheet layer;

a liquid permeable topsheet layer;

an absorbent structure sandwiched between said backsheet and topsheet layers; and a fastening system for connecting said first waistband portion to said second waistband portion to hold said article on a wearer, said fastening system including at least one fastener tab attached to extend laterally at a side edge region of said first waistband portion, and an articulating landing member joined to said second waistband portion;

said fastener tab including an extending layer member having a clasping contour formed therein, said clasping contour provided by at least one indentation formed into a longitudinal side edge of said layer member of said fastener tab;

said landing member having a movable section pivotably attached to said second waistband portion of the article, and a first fastener component attached to an appointed mating surface of said movable section; and said second waistband portion having a cooperating second fastener component attached to an appointed engagement surface section of said second waistband portion, said engagement surface section located substantially subjacent said movable section of the landing member, wherein said first fastener component is interengageable with said second fastener component through open areas exposed by at least a portion said clasping contour to trap said fastener tab between said first fastener component and said second fastener component when said first fastener component and said second fastener component are interengaged.

2. The article as recited in claim 1, wherein said first waistband portion is configured to provide an overlapping relation with said second waistband portion when said article is worn; and said engagement surface section of the second waistband portion is an outward surface of said waistband portion.

3. The article as recited in claim 1, wherein said landing member includes a base section which is attached to said outward surface of said second waistband portion, and wherein said movable section is pivotably attached to said base section.

4. The article as recited in claim 1, wherein at least one fastening tab is attached to extend laterally at each of a pair of laterally opposed side edge regions of said first waistband portion, and a laterally opposed pair of landing members are attached to said second waistband portion.

5. The article as recited in claim 4, wherein a composite landing member provides said laterally opposed pair of landing members with a substantially contiguous, interconnected configuration.

6. The article as recited in claim 5, wherein said composite landing member includes a cap member, said cap member having a medial region attached to said second waistband portion of the article, and a pair of movable wing sections which are pivotably attached to said medial region of the cap member, and wherein an area of said first mechanical fastener component is attached to an appointed mating surface of each said movable wing section.

7. The article as recited in claim 6, wherein said composite landing member includes a carrier member attached to said second waistband portion of the article and interposed between said cap member and said backsheet layer, said carrier member including a medial region thereof which is attached to said medial region of said cap member, and wherein an area of said second mechanical fastener component is attached to an outward surface of a laterally opposed pair of end regions of said carrier member.

8. The article as recited in claim 7, wherein said pair of end regions of said carrier member are attached to said second waistband portion of the article.

9. The article as recited in claim 7, wherein said pair of end regions of said carrier member are substantially unattached to said second waistband portion of the article.

10. The article as recited in claim 1, wherein said first fastener component includes a first mechanical fastening component which includes a hook material.

11. The article as recited in claim 10, wherein said second fastener component includes a second mechanical fastening component which includes a loop material.

12. The article as recited in claim 1, wherein said first mechanical fastening component is a loop material.

13. The article as recited in claim 12, wherein said second mechanical fastening component is a hook material.

14. The article as recited in claim 1, wherein said first mechanical fastener component is configured to operably engage said second mechanical fastener component within and through said clasping contour when said mating surface of said movable section is positioned in a mating relation with said appointed outward surface section of said second waistband portion.

15. The article as recited in claim 1, wherein said clasping contour is provided by at least one aperture formed through said fastener tab layer member.

16. The article as recited in claim 1, wherein said clasping contour is provided by a plurality of apertures formed through said fastener tab layer member.

17. The article as recited in claim 1, wherein said clasping contour is provided by a plurality of indentations formed into longitudinal side edges of said fastener tab layer member.

18. An absorbent article having a first waistband portion, a second waistband portion and an intermediate portion interconnecting said front and back waistband portions, said article comprising:

a backsheet layer;

a liquid permeable topsheet layer;

an absorbent structure sandwiched between said backsheet and topsheet layers; and a fastening system for connecting said first waistband portion to said second waistband portion to hold said article on a wearer, said fastening system including at least one fastener tab attached to extend laterally at a side edge region of said first waistband portion, and an articulating landing member joined to said second waistband portion;

said fastener tab including an extending layer member having a clasping contour formed therein, said clasping contour is provided by at least one aperture formed through said fastener tab layer member and by side edges of said fastener tab layer member;

said landing member having a movable section pivotably attached to said second waistband portion of the article, and a first fastener component attached to an appointed mating surface of said movable section; and said second waistband portion having a cooperating second fastener component attached to an appointed engagement surface section of said second waistband portion, said engagement surface section located substantially subjacent said movable section of the landing member, wherein said first fastener component is interengageable with said second fastener component at areas of said first and second fastener components that are exposed by said at least one aperture and side edges to trap said fastener tab between said first fastener component and said second fastener component when said first fastener component and said second fastener component are interengaged.

19. The article as recited in claim 18, wherein said clasping contour includes a plurality of apertures formed through said fastener tab layer member.

20. An absorbent article having a first waistband portion, a second waistband portion and an intermediate portion interconnecting said front and back waistband portions, said article comprising:

a backsheet layer;

a liquid permeable topsheet layer;

an absorbent structure sandwiched between said backsheet and topsheet layers; and a fastening system for connecting said first waistband portion to said second waistband portion to hold said article on a wearer, said fastening system including at least one fastener tab attached to extend laterally at a side edge region of said first waistband portion, and an articulating landing member joined to said second waistband portion;

said fastener tab including an extending layer member having a clasping contour formed therein, said clasping contour provided by side edges of said fastener tab layer member and by at least one indentation formed into a longitudinal side edge of said fastener tab layer member;

said landing member having a movable section pivotably attached to said second waistband portion of the article, and a first fastener component attached to an appointed mating surface of said movable section; and said second waistband portion having a cooperating second fastener component attached to an appointed engagement surface section of said second waistband portion, said engagement surface section located substantially subjacent said movable section of the landing member, wherein said first fastener component is interengageable with said second fastener component through areas of said first and second fastener components that are exposed along said side edges and said at least one indentation to trap said fastener tab between said first fastener component and said second fastener component when said first fastener component and said second fastener component are interengaged.

21. The article as recited in claim 20, wherein said clasping contour is provided by a plurality of indentations formed into longitudinal side edges of said fastener tab layer member; and said first fastener component is interengageable with said second fastener component through areas exposed along said side edges and said plurality of indentations to trap said fastener tab between said first fastener component and said second fastener component when said first fastener component and said second fastener component are interengaged.

22. The article as recited in claim 20, wherein said clasping contour includes at least one aperture formed through said fastener tab layer member.

23. The article as recited in claim 20, wherein said clasping contour includes a plurality of apertures formed through said fastener tab layer member.

* * * * *